United States Patent

Gilman et al.

[11] Patent Number: 5,935,363
[45] Date of Patent: Aug. 10, 1999

[54] PROCESS FOR MAKING CONTOURED HYDROCOLLOID-CONTAINING ADHESIVE DRESSINGS

[75] Inventors: Thomas H. Gilman, Spring Grove; Eric D. Ellingson, Mount Prospect, both of Ill.

[73] Assignee: Hollister Incorporated, Libertyville, Ill.

[21] Appl. No.: 08/889,685

[22] Filed: Jul. 8, 1997

Related U.S. Application Data

[63] Continuation-in-part of application No. 08/678,224, Jul. 11, 1996, abandoned.

[51] Int. Cl.⁶ .............................. A61F 13/02; B29C 43/02; B29C 43/20; B29C 47/00
[52] U.S. Cl. .................. 156/199; 156/220; 156/244.18; 156/244.25; 156/244.27; 156/269; 156/289; 156/324; 264/163; 264/241; 264/257
[58] Field of Search ...................................... 156/199, 209, 156/220, 244.11, 244.18, 244.25, 244.27, 246, 247, 267, 269, 289, 323, 324; 264/163, 241, 257, 297.1, 299, DIG. 8; 602/56, 57, 58; 604/336, 344

[56] References Cited

U.S. PATENT DOCUMENTS

| | | |
|---|---|---|
| 3,822,161 | 7/1974 | Haase . |
| 3,824,761 | 7/1974 | Wright . |
| 4,340,557 | 7/1982 | Gross . |
| 4,367,732 | 1/1983 | Poulsen et al. . |
| 4,622,089 | 11/1986 | Lauritzen . |
| 4,693,858 | 9/1987 | Volke . |
| 4,780,168 | 10/1988 | Beisang et al. . |
| 4,823,783 | 4/1989 | Willhite et al. . |
| 4,867,748 | 9/1989 | Samuelsen . |
| 4,867,821 | 9/1989 | Morgan . |
| 5,006,189 | 4/1991 | Tsukamoto et al. . |
| 5,074,944 | 12/1991 | Trenka . |
| 5,133,821 | 7/1992 | Jensen . |
| 5,201,976 | 4/1993 | Eastin . |
| 5,405,486 | 4/1995 | Sablotsky et al. . |

*Primary Examiner*—Richard Crispino
*Attorney, Agent, or Firm*—Tilton Fallon Lungmus

[57] ABSTRACT

A process is disclosed for making contoured hydrocolloid-containing adhesive dressings in which, in the final product, a soft pliant adhesive layer having one or more hydrocolloids dispersed therein is sandwiched between a top backing layer of stretchable film or fabric and a bottom release layer of flexible but substantially non-stretchable material. In a combined contouring and cutting step, the layers are compressed and heated to reshape the adhesive material and are simultaneously cut to form the finished dressing. In a preferred embodiment, three steps of laminating, contouring and cutting are performed simultaneously at a single station.

13 Claims, 2 Drawing Sheets

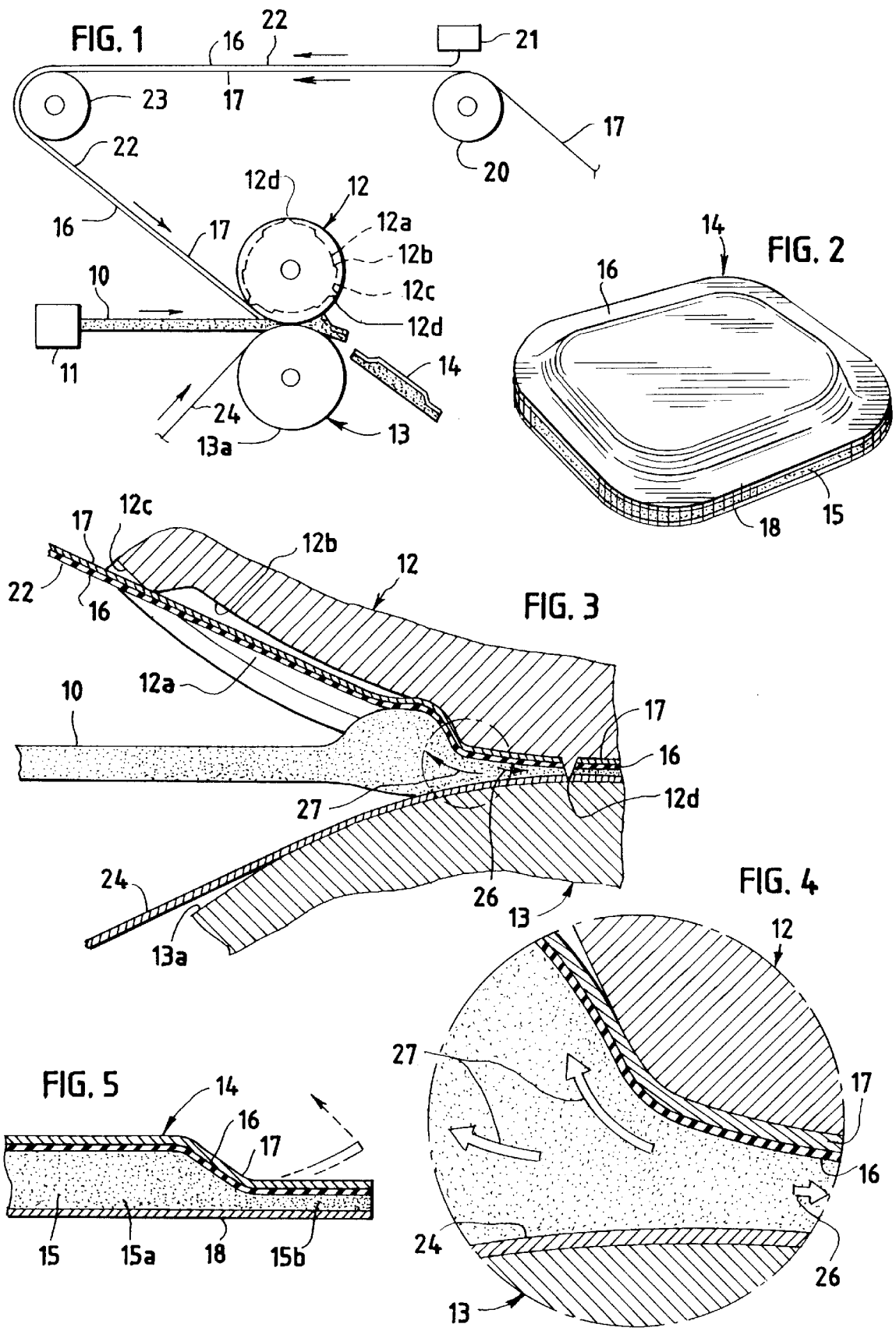

5,935,363

PROCESS FOR MAKING CONTOURED HYDROCOLLOID-CONTAINING ADHESIVE DRESSINGS

RELATED APPLICATION

This application is a continuation-in-part of our copending application Ser. No. 08/678,224, filed Jul. 11, 1996 and now abandoned.

BACKGROUND AND SUMMARY

Jensen U.S. Pat. No. 5,133,821 and Samuelsen U.S. Pat. No. 4,867,748 disclose dressings having adhesive layers of hydrocolloid-containing materials with upper surfaces protected by covering layers, preferably of elastomeric film, and undersurfaces protected by removable release sheets. The Samuelsen patent suggests that such a contoured dressing may be made by a pressing and molding operation using blanks in which the three layers are pre-laminated together and, following the molding step, the blanks are then die cut in a conventional manner. The Jensen patent discloses a continuous method in which contoured dressings are produced by advancing webs of material through three successive operating stations.

In the first operating station of the Jensen patent, a strip of adhesive material containing hydrocolloids, and supported upon a release web, is contoured between a pair of rollers. According to the patent, the upper contouring roller may be coated with a release agent to prevent it from sticking to the adhesive material but, in a preferred embodiment, a web of silicone-coated release paper is interposed between the contouring roller and the adhesive material. The release paper is sacrificial and is removed from the adhesive layer in a delaminating step following the contouring step. Thereafter, the adhesive surface of each partially-formed dressing is covered by a so-called adhesive carrier layer in a second laminating station, the adhesive carrier layer thereby taking the place of the removed paper layer used in the contouring step. Finally, the second laminate advances from the laminating station to a cutting station where the finished dressings are cut into final shape between a pair of cutting rollers.

The Jensen patent does not elaborate on why it is important that the contouring, laminating and cutting steps be carried out in three successive stations and, in particular, why it is critical that contouring be completed before the adhesive carrier layer is applied to the exposed surface of the adhesive layer. Experience has shown that the sequence is indeed important and that if the adhesive carrier layer (i.e., the backing layer) is a thin elastomeric film, it is not suitable for use as the release web in the contouring station for purposes of preventing the contouring roller from adhering to the adhesive layer. Hence, in a continuous process for making hydrocolloid dressings, the prior art has emphasized the necessity of having successive stations for contouring, laminating, and cutting, with the complexities in equipment and timed operation that such a system inherently require.

Other references revealing the state of the art are U.S. patents to Gross U.S. Pat. No. 4,340,557, Morgan U.S. Pat. No. 4,867,821, Lauritzen U.S. Pat. No. 4,622,089, Eastin U.S. Pat. No. 5,201,976, Tsukamoto et al U.S. Pat. No. 5,006,189, Willhite et al U.S. Pat. No. 4,823,783, Beisang et al U.S. Pat. No. 4,780,168, Trenka U.S. Pat. No. 5,074,944, Wright U.S. Pat. No. 3,824,761 and Volke U.S. Pat. No. 4,963,858.

A main aspect of this invention therefore lies in the discovery, that, contrary to the teachings of the prior art, it is indeed possible to make contoured hydrocolloid wound dressings in an operation in which at least the contouring and cutting steps are combined, and preferably the laminating, contouring and cutting steps are combined, with such steps being performed simultaneously to produce a highly effective product in which a stretchable backing layer covers the contoured adhesive surface of the dressing without wrinkles and deformations. A further aspect of the invention lies in the discovery that such steps may be combined at a single operating station to produce a product free of wrinkles and deformations if the backing layer is restrained against stretching along the general plane of the product being formed, or the simultaneous processing steps are carried out in a manner to avoid such stretching, as the hydrocolloid-containing adhesive material is displaced to form the contoured product.

Avoidance of stretching of the backing material in the plane of the dressing allows the contouring step to be combined with the cutting step and, preferably, with the laminating step, all at a single operating station. The steps taken to avoid such stretching of the backing layer during processing depend on factors such as the stretchability, recoverability and thickness of the backing material selected, the flowability and adhesiveness of the hydrocolloid-containing material, and the temperature at which the operation is performed. In general, it has been found that the backing layer must be able to resist stretching along the plane of the dressing (as exemplified by the plane of the flat release sheet or web) in response to shear forces exerted by the hydrocolloid-containing adhesive material as that material is forced to flow outwardly and/or inwardly under compression. Where the backing material is highly stretchable and would be incapable of resisting such stretching action in response to the outward/inward flow of the adhesive material in a contouring operation, it has been found that stretching of the backing layer may be prevented by removably attaching to it a flexible and substantially non-stretchable reinforcing layer. Ideally, if the stretchable backing layer is a film, then the reinforcing layer may also provide the surface on which the film was originally cast.

Another aspect of the invention lies in the further discovery that the three operations—laminating, contouring and cutting—may be performed simultaneously by the same contouring, laminating and cutting dies. Preferably, such dies are in the form of rollers, although it is possible that the contouring and cutting operations may be performed simultaneously at one station by a pair of reciprocating plates and the laminating operation performed either at the same station or immediately adjacent to it.

Other features, advantages, and objects of the invention will become apparent from the specification and drawings.

DRAWINGS

FIG. 1 is a diagramatic and schematic view depicting a preferred embodiment of the process of this invention.

FIG. 2 is a perspective view of a contoured dressing made by the process of FIG. 1.

FIG. 3 is a fragmentary sectional view depicting the action that occurs between the upper and lower contouring/laminating/cutting rollers used in the process of this invention.

FIG. 4 is a still further enlarged sectional view of the area encircled in phantom in FIG. 3.

FIG. 5 is an enlarged fragmentary sectional view of a contoured dressing made in accordance with the invention.

DETAILED DESCRIPTION OF PREFERRED EMBODIMENTS

Figure 6:
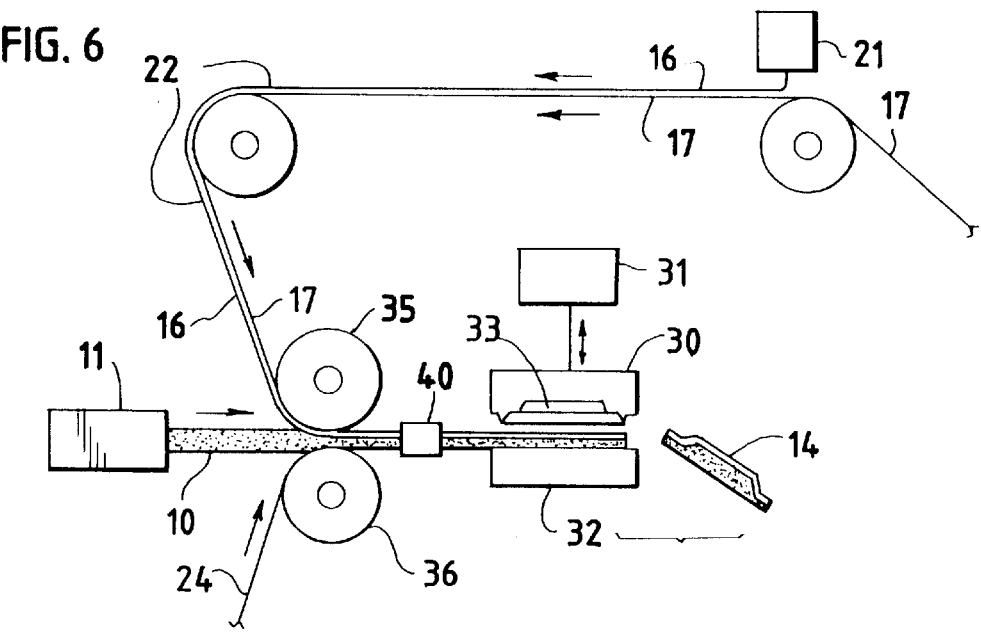
FIG. 6 is a diagramatic and schematic view depicting a second embodiment of the process of this invention.

Referring to the embodiment depicted in FIGS. 1, 3 and 4, a continuous strip 10 of soft, pliant, hydrocolloid-containing adhesive material is discharged from extruder 11 and enters the nip between upper and lower rollers 12 and 13. The rollers are power driven with the lower roller 13 serving as a rotating anvil having a substantially smooth outer surface 13a. The upper roller 12 functions as a contoured laminating, contouring and cutting die and has a developed or shaped surface defining recesses 12a with relatively deep central portions 12b and relatively shallow peripheral portions 12c. Cutting blades 12d surround the peripheral portions, with the length of the blades being sufficient to contact anvil roller 13 to perform a cutting operation as depicted in FIG. 3. In the diagramatic and schematic view of FIG. 1, the upper roller 12 is shown to have three such recesses 12a; however, it is to be understood that a different number may be provided and that the shapes of the recesses (or, if desired, protrusions) may be varied depending on the particular contour of the dressing to be produced.

FIG. 1 depicts a contoured dressing 14 as it is released from the laminating/contouring/cutting station. A portion of such a dressing is illustrated in section in FIG. 5 where it will be seen that the dressing has a hydrocolloid adhesive layer 15 derived from the extruded adhesive strip 10. The adhesive layer 15 has a relatively thick central body portion 15a and a thin peripheral flange portion 15b. A stretchable backing layer 16 of film or fabric covers the contoured surface of adhesive layer 15, and a removable reinforcing layer 17 of flexible but relatively stiff and non-stretchable material covers the backing layer 16. The underside of the dressing 14 is protected by a removable release sheet 18 of siliconized paper or other suitable material.

While dressing 14 has been described in completed form in connection with FIG. 5, a final step must be undertaken either by the manufacturer or user before the dressing is ready for use. The removable reinforcing layer 17 must be peeled away from the backing layer 16 as indicated in broken lines in FIG. 5. FIG. 2 illustrates the dressing 14 with the reinforcing layer 17 removed, revealing the stretchable upper backing layer 16 and the edges of the adhesive layer 15 and release paper layer 18. It is to be understood that at the time the dressing is to be used, the planar release layer 18 is peeled away from the underside of the adhesive layer to expose the adhesive layer for contact with the skin over and about an attachment site.

The term "dressing" is here used to refer to hydrocolloid-containing wound dressings as well as dressings more commonly referred to as hydrocolloid adhesive wafers or faceplates for ostomy appliances. Reference may be had to U.S. Pat. No. 4,867,748 for examples of the general use of this term.

Adhesive material 15 may be of any of a variety of hydrocolloid-containing adhesive compositions well known in the art. In general, such material comprises a tacky semi-solid binder in which particles of one or more hydrocolloids are dispersed. Although polyisobutylene is preferred as the binder, other viscous semi-solid adhesive materials may be used such as, for example, styrene block polymer rubbers, silicone rubber, acrylonitrile rubber, polyurethane rubber and natural rubber (caoutchouc). The hydrocolloid content is commonly a blend of hydrocolloids such as carboxymethylcellulose, pectin, guar gum and/or gelatin, but other hydrocolloids such as karaya, polyvinyl alcohol, carbowax and carboxypolymethylene have been disclosed in the literature and may be used. For further information concerning such hydrocolloid-containing adhesive compositions, and citations of other background materials relating thereto, reference may be had to co-owned U.S. Pat. No. 4,738,257.

A suitable material for backing layer 16 is a thin film of a nylon/polyether block polymer elastomer (PEBAX resin from ATO, Philadelphia, Pa.) but polyurethane or other polymers having similar properties may be used. An elastomeric film having a thickness within the range of about 0.5 to 1.5 mils is believed particularly suitable. Films of silicone rubber and latex rubber may also be effective. Further, the backing layer may be an elastomeric or stretchable fabric, such as a non-woven fabric. Stretchable non-woven microporous fabrics composed of polyethylene fibers are known and may be used, for example, the microporous fabric marketed under the designation MF5260 by Freudenberg Nonwovens LP, Halifax, England and other stretchable fabrics having similar properties are believed suitable.

While films that are highly stretchable are often elastomeric in character, the problems to which this invention is addressed arise largely because of the stretchability of the backing layer 16 rather than the extent of its recovery after stretching forces are removed. Therefore, the term "stretchable" is preferably and more accurately used here to describe the physical characteristic of the backing film or fabric, and it is the prevention or restraint of such stretching of the backing layer 16 by the non-stretchable and removable reinforcing layer 17 that is particularly important in this process.

The purpose of reinforcing layer 17 is to restrain stretching of the backing layer 16 in planar directions in response to the flow of adhesive material (in the directions of arrows 26 and 27) during the contouring operation. If displacement of the adhesive material under pressure during contouring is accompanied by stretching of backing layer 16, then objectionable wrinkling and deformation of the backing layer is likely to occur and be present in the resulting dressings. It is at the interface between backing layer 16 and pliant adhesive layer 15 that the forces tending to stretch the backing layer are transmitted so that if such forces are insufficient to cause stretching of the backing layer in the absence of the reinforcing layer, then such reinforcement becomes unnecessary. Thus, reinforcing layer 17 may be omitted if the backing layer 16, although necessarily formed of stretchable material, does not stretch in planar directions (in response to displacement of adhesive material during contouring) either because of the composition or thickness of the backing layer or because the forces at the interface are insufficient to result in stretching of the backing layer by reason of factors such as the composition, temperature and/or flow characteristics of the adhesive material.

Use of reinforcing layer 17 is therefore optional in those instances where it is not required for purposes of preventing stretching of the backing layer 16 during a combined laminating/contouring/cutting operation as generally depicted in FIGS. 1 and 3. When used, reinforcing layer 17 must be flexible but nevertheless relatively stiff, especially when compared with the film or fabric backing layer 16. Layer 17 may be capable of being deformed or embossed, but an essential characteristic is that it must be substantially non-stretchable. A strong paper is believed particularly suitable, but other materials, such as flexible but substantially non-stretchable polymeric films, may also be used. Where the stretchable layer 16 takes the form of an elastomeric film, the reinforcing layer 17 is most advantageously formed of sheet material on which the film has been deposited by conventional extruding or solvent-casting techniques. In such a case, a polyolefin-coated paper (for example, a polyolefin-coated paper from Schoeller Technical Papers, Pulaski, N.Y.) is especially suitable for use as reinforcing layer 17.

A substantially continuous supply of a reinforcing web 17 is provided from a supply roll (not shown) and is directed over guide roll 20 to extruder 21 (FIG. 1). The stretchable backing material 16 in the form of a thin layer is discharged by the extruder onto layer 17, and the two continue together as a combined backing web 22 about guide roller 23 to the laminating/contouring/cutting station where the combined web enters the nip between upper and lower rollers 12 and 13 along the upper surface of the extruded strip 10 of adhesive material. At the same time, a web of release sheet material 24 from a supply roll (not shown) enters the nip beneath the extruded strip 10. The extruded strip and the two webs merge together to form a laminate which is simultaneously contoured (and cut) between the rollers as determined by the surface of contouring roller 12.

During such operation, the viscous hydrocolloid-containing adhesive material should be maintained at a temperature that promotes the flow of such material under pressure. Such a result may be achieved by heating rollers 12 and 13. The temperature may vary depending on the composition of the adhesive material involved but, in general, temperatures within the range of about 120 to 220° F. are believe suitable. As an alternative to heating the rollers, or in addition thereto, the strip 10 of adhesive material may be passed through a preheating zone in advance of rollers 12 and 13, although such preheating may be unnecessary if the distance between the rollers and the extruder is relatively short.

At lower temperatures within the range indicated, a rebound effect may be observed, as described below, and that effect tends to become diminished as temperatures are increased. In FIG. 3, it will be noted that the leading portion of cutting edge 12d of the upper roller 12 has already contacted the surface of the lower anvil roller 13, serving as a dam to limit forward displacement of the adhesive material of extruded strip 10 in the direction of arrow 26 in FIG. 4. Substantial backflow occurs in the direction of arrows 27, causing the hydrocolloid-containing adhesive material to expand or flow into the recess 12b of the contouring roller 12. Since the soft and heated adhesive material is not only deformable but compressible to at least a limited extent, release of compressive force as the materials pass through the nip tends to be accompanied by a slight expansion in the thickness of the dressing beyond the dimensions established by the spacing between the rollers.

Substantial flow of adhesive material occurs as indicated by arrows 26 and 27 in FIGS. 3 and 4, and such flow imparts considerable force on the backing film or fabric 16. The reinforcing layer 17, when needed and used, resists such forces that would otherwise stretch, distort and displace the thin backing layer 16. If movement of the backing layer relative to the reinforcing layer were free to occur, noticable deformation and distortion would result and, especially if the backing layer were elastomeric as well as stretchable, wrinkling of the backing layer would also take place as the stretched elastomer at least partially recovers or retracts following the laminating/contouring/cutting steps. Unacceptable warping and distortion of the dressing in other respects could also result. However, the frictional forces, or forces of adhesion, between the stretchable backing layer 16 and the reinforcing layer 17 exceed the forces exerted on the backing layer by the adhesive material as it is displaced in the directions of arrows 26 and 27, and the strength of the reinforcing layer 17 (aided by the support for that layer provided by the contoured roller) resists tearing of the reinforcing layer, during a contouring operation. Consequently, the reinforcing layer serves to prevent significant stretching of the backing layer 16 and the aforementioned problems of deformation, distortion and wrinkling are thereby avoided.

Figure 7:
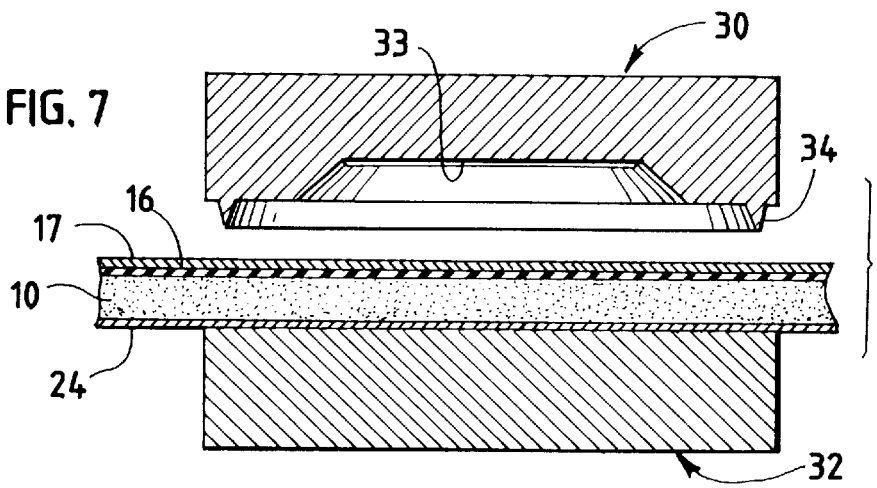
FIG. 7 is an enlarged sectional view illustrating the contouring mold and anvil platen of the second embodiment in open condition.
Figure 8:
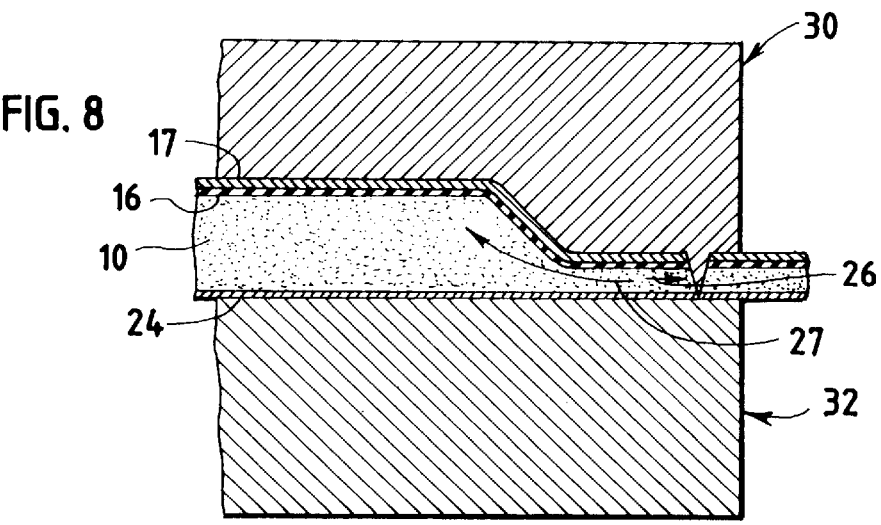
FIG. 8 is a view similar to FIG. 7 but showing the mold and platen in closed condition.

In the embodiment of FIGS. 6–8, the process is similar to the one already described except that a vertically movable contouring/cutting die and an anvil platen rather than rollers are provided at the contouring and cutting station. Also, lamination does not occur simultaneously at the contouring/cutting station but immediately in advance of that station.

Specifically, a movable upper plate or die 30 carried by reciprocating mechanism 31 is located above stationary lower platen 32. The upper plate is recessed at 33 to serve as a shaped contouring die and is provided with cutting edges 34. Lower platen 32 serves as a supporting anvil. As in the previous embodiment, both the upper and lower elements 30 and 32 are heated, or other means provided to insure that the adhesive material is properly heated at the contouring/cutting station.

A strip of extruded hydrocolloid-containing adhesive material 10 is discharged from extruder 11 and enters the nip between upper and lower power-driven laminating rollers 35 and 36. Lamination of the adhesive material 10 with the combined backing web 22 (composed of stretchable backing layer 16 and non-stretchable reinforcing layer 17) and with release web 24, occurs between rollers 35 and 36 immediately in advance of the contouring/cutting station. (As previously noted, the use of reinforcing layer 17 is optional in those instances where the backing layer 16, although stretchable, is not so highly stretchable that reinforcement to prevent stretching during contouring is necessary.) FIG. 6 and 7 depict the laminate as it enters the contouring/cutting station with die 30 in its raised or open position, and FIG. 8 is a fragmentary view showing die 30 in its lowered position. The flow of heated adhesive material is again indicated by arrows 26 and 27 and is similar to that occurring in the process of the first embodiment.

Unlike the continuous operation of the first embodiment however, the advancement of a laminate at the contouring/cutting station must be intermittent because of the reciprocating operation of the upper die 30. Since the operation of the extruder 11 is continuous rather than intermittent, a conventional web accumulation bank 40, diagramatically shown in FIG. 6, should be interposed between the rollers 35, 36 and the contouring/cutting station to take up slack that would otherwise develop in the web by reason of the non-continuous or interrupted movement of the laminate into and through the contouring/cutting station.

The arrangement of FIGS. 6–8, in which a lamination step occurs in advance of the contouring/cutting station, may also be utilized in a system that includes contouring and cutting rollers of the first embodiment in place of the upper and lower plates of the second embodiment, but in such a case it is believed desirable for the adhesive strip and the release web to be brought together at the advance lamination station and later joined or laminated to the stretchable backing at the contouring/cutting station.

In all embodiments of the invention, contouring and cutting occurs simultaneously at the same station, whether by rollers 12, 13 or by plates 30, 32. In addition to the operating efficiencies and reduced spatial requirements so achieved, proper registry or concentricity of contouring and cutting for each dressing is assured, thereby avoiding or greatly reducing wastage of expensive materials (especially hydrocolloid-containing adhesive materials) that is known to occur when such steps are performed successively at different stations and some proportion of the dressings so produced must be discarded because proper registry is lacking.

While in the foregoing, we have disclosed embodiments of the invention in considerable detail for purposes of illustration, it will be understood by those skilled in the art that many of these details may be varied without departing from the spirit and scope of the invention.

We claim:

1. A process for making contoured dressings having a hydrocolloid-containing adhesive layer disposed between a stretchable backing layer and a planar release layer, comprising the steps of providing an adhesive layer in the form of a substantially continuous adhesive strip of a soft, pliant adhesive material flowable under pressure and having at least one liquid-absorbing hydrocolloid material dispersed therein; providing a substantially continuous supply of a backing web comprising a backing layer of stretchable material; providing a release layer in the form of a substantially continuous supply of a release web; merging said backing web with said adhesive strip and said release web by advancing the same through a nip between a first roller in contact with said backing web and a second roller in contact with said release web; said first roller having a shaped surface defining recesses with cutting edges surrounding said recesses; said backing web, adhesive strip, and release web being merged between said rollers to form a laminate in which said backing web has its layer of stretchable material in contact with one side of said adhesive strip and said release web is in contact with the strip's opposite sides and applying pressure by means of said rollers to the laminate, without stretching said backing layer of stretchable material in planar directions, to contour the backing layer and adhesive material of said laminate while simultaneously cutting said laminate by said rollers as said laminate is being contoured to form discrete dressings of predetermined size and shape.

2. The process of claim 1 in which said stretchable backing layer of said backing web comprises an elastomeric film.

3. The process of claim 1 in which said stretchable backing layer is of non-woven material.

4. The process of claim 1 in which said backing web includes a reinforcing layer of flexible and substantially non-stretchable material removably attached to the surface of said stretchable backing layer facing away from said adhesive strip.

5. The process of claim 4 in which there is the further step of stripping said layer of reinforcing material away from the stretchable backing layer of each dressing after the dressings are contoured and cut.

6. The process of claim 4 in which said reinforcing layer comprises a stiff paper having a release coating on the side thereof facing said stretchable backing layer.

7. A process for making contoured dressings having a hydrocolloid-containing adhesive layer disposed between a stretchable backing layer and a generally planar release layer, comprising the steps of forming a substantially continuous backing web comprising a backing layer of stretchable material reinforced by and removably attached to a flexible and substantially non-stretchable reinforcing layer; providing an adhesive layer in the form of a substantially continuous adhesive strip of soft, pliant adhesive material flowable under pressure and having liquid-absorbing hydrocolloid particles dispersed therein; providing a release layer in the form of a substantially continuous release web; merging said adhesive strip, said backing web, and said release web in a laminating step in which the same are advanced through a nip between a first roller in contact with said backing web and a second roller in contact with said release web; said first roller having a shaped surface defining recesses with cutting edges surrounding said recesses; said backing web, adhesive strip, and release web being merged between said rollers to form a laminate in which said backing web has its backing layer of stretchable material in contact with one side of said adhesive strip and said release web is in contact with the strip's opposite side; and applying pressure to the laminate by means of said rollers to contour said backing layer and adhesive material of said laminate while simultaneously cutting said laminate by said rollers as said laminate is being contoured to form discrete dressings of predetermined size and shape.

8. The process of claim 7 in which said step of forming said backing web comprises depositing said layer of stretchable material onto a surface of said reinforcing layer.

9. The process of claim 8 in which said stretchable material is solvent cast onto said reinforcing layer.

10. The process of claim 8 in which said layer of stretchable material is extruded onto said reinforcing layer.

11. The process of claim 7 in which said stretchable layer of said backing web comprises an elastomeric film.

12. The process of claim 7 in which said stretchable layer of said backing web is a non-woven fabric.

13. The process of claim 7 in which there is the further step of stripping said layer of reinforcing material away from the stretchable backing layer of each dressing.

* * * * *